United States Patent [19]

Casale

[11] Patent Number: 5,310,407
[45] Date of Patent: May 10, 1994

[54] LAPAROSCOPIC HEMOSTAT DELIVERY SYSTEM AND METHOD FOR USING SAID SYSTEM

[75] Inventor: John Casale, Oakland, N.J.

[73] Assignee: Datascope Investment Corp., Montvale, N.J.

[21] Appl. No.: 968,262

[22] Filed: Oct. 30, 1992

Related U.S. Application Data

[63] Continuation of Ser. No. 716,837, Jun. 17, 1991, abandoned.

[51] Int. Cl.$^5$ .......................... A61M 31/00
[52] U.S. Cl. ............................ 604/51; 604/59; 604/60
[58] Field of Search .......... 604/57, 60, 59, 61, 604/218, 48, 15, 51, 28

[56] References Cited

U.S. PATENT DOCUMENTS

| | | | |
|---|---|---|---|
| 3,016,895 | 1/1962 | Sein | 128/217 |
| 3,572,335 | 3/1971 | Robinson | 128/217 |
| 4,578,061 | 3/1986 | Lemelson | 604/164 |
| 4,588,395 | 5/1986 | Lemelson | 604/59 |
| 4,619,261 | 10/1986 | Guerriero | 128/325 |
| 4,638,803 | 1/1987 | Rand | 128/325 |
| 4,744,364 | 5/1988 | Kensey | 128/334 R |
| 4,749,689 | 6/1988 | Miyata et al. | 514/21 |
| 4,790,819 | 12/1988 | Li et al. | 604/59 |
| 4,852,568 | 8/1989 | Kensey | 128/325 |
| 4,878,906 | 11/1989 | Lindemann et al. | 623/1 |
| 4,890,612 | 1/1990 | Kensey | 606/213 |
| 4,900,303 | 2/1990 | Lemelson | 605/54 |
| 4,929,246 | 5/1990 | Sinofosky | 606/8 |
| 4,941,874 | 7/1990 | Sandow et al. | 604/60 |
| 4,950,234 | 8/1990 | Fujioka et al. | 604/60 |
| 4,994,028 | 2/1991 | Leonard et al. | 604/60 |
| 5,021,059 | 6/1991 | Kensey et al. | 606/213 |
| 5,061,274 | 10/1991 | Kensey | 604/15 |
| 5,063,025 | 11/1991 | Ito | 604/218 |
| 5,141,515 | 8/1992 | Eberbach | 606/151 |

FOREIGN PATENT DOCUMENTS

| | | |
|---|---|---|
| 89073703 | 9/1989 | Fed. Rep. of Germany . |
| 2641692 | 7/1992 | France . |
| 91-07425 | 4/1992 | PCT Int'l Appl. . |
| 91-07601 | 4/1992 | PCT Int'l Appl. . |
| 89/11301 | 11/1989 | World Int. Prop. O. . |

OTHER PUBLICATIONS

Peters, et al., "What's New In General Surgery: Safety and Efficacy of Laparoscopic Cholecystectomy: A Prospective Analysis of 100 Initial Patients", Annals of Surgery, vol. 213(1) (Jan. 1991) (pp. 3-12) (Reprinted from computer database).

Kent and Naughton, "Brief Clinical Report; Hemostasis of the Gallbladder Fossa During Laparoscopic Cholecystectomy" Surgery Laparoscopy & Endoscopy, vol. 1, No. 2, pp. 104-105 (Jun. 1991).

Arnoczky, et al., "Meniscal Repair Using an Exogenous Fibrin Clot; An Experimental Study In Dogs," Journal of Bone & Joint Surgery, pp. 1209-1217 (1988).

Datascope Corp. Package Insert: "Astra Hemopad TM Absorbable Collagen Hemostat" (1986).

*Primary Examiner*—Paul J. Hirsch
*Attorney, Agent, or Firm*—Fitzpatrick, Cella, Harper & Scinto

[57] ABSTRACT

A delivery system and method for inserting hemostatic material through a channel of a laparoscopic cannula, and for directly applying the material to an internal tissue site, includes a hollow sheath having a cross-section and configuration that permits sliding passage thereof through the channel of the laparoscopic cannula. The sheath is charged with hemostatic material, and the hemostatic material is advanced through the lumen of the sheath and mechanically applied at the tissue site by an applicator. The hemostatic material may be in the form of compressed loose fibers, a sponge, a powder, a paste, a sheet, or a combination thereof, and may be composed of resorbable collagen.

15 Claims, 1 Drawing Sheet

LAPAROSCOPIC HEMOSTAT DELIVERY SYSTEM AND METHOD FOR USING SAID SYSTEM

This application is a continuation of application Ser. No. 07/716,837 filed Jun. 17, 1991, now abandoned.

BACKGROUND OF THE INVENTION

1. Field of the Invention

The present invention relates generally to laparoscopic and similar surgical procedures, and more particularly to a hemostat delivery system and method for using same in a laparoscopic procedure.

2. Description Of The Prior Art

Laparoscopic, arthroscopic and endoscopic cannulae and surgical procedures are known. Initially, it should be understood that the delivery system of the present invention is independent of the nature of the specific medical procedure being performed. Thus, "laparoscope" is used here as a generic term which is meant to encompass other similar type devices including the arthroscope and endoscope. Similarly, references herein to a "laparoscopic" procedure should be understood as encompassing "arthroscopic" and "endoscopic" procedures as well.

Normally, preparatory to initiating a laparoscopic procedure, several cannulae are inserted into the body. These cannulae serve as channels through which various instruments are inserted One generally serves to pass the laparoscope itself (i.e., the fiber optic device which carries light to the site for illumination and back from it for viewing) Another can serve as the gas delivery/ventilating channel and the rest will generally serve as working channels to pass the implements used to perform the procedure.

Laparoscopes have been employed to perform a wide range of surgical procedures. Many of these procedures can result in a considerable amount of internal bleeding. For example, recently a laparoscopic procedure has been developed for removing gall bladders, which procedure requires severing the vascularized stem containing the artery that supplies blood to the gall bladder as well as numerous arterioles, venuoles, and capillaries. The larger, major vessels are ligated or tied off via clips introduced through a working channel or otherwise, and cautery is used to seal off any remaining bleeding of the ligated vessels and as much of the bleeding "bed" as possible. Cautery has its own risks and limitations which can include incomplete or irregular sealing of vessels and which can contribute to problems of postoperative bleeding, one of the three most significant complications of the procedure. In order to avoid the drawbacks of cauterization and other similar procedures, the present invention uses collagen.

Of course, it is well known to use collagen to stanch bleeding. Specifically, in traditional surgical procedures, hemostasis initially is achieved by mechanical means, i.e., collagen is applied with direct mechanical pressure around the bleeding site. Immediately, the collagen material begins to interact with clotting elements in the blood and tissue of the site and initiates biochemical hemostasis. Once the hemostasis becomes sufficiently strong, e.g., strong enough to withstand blood pressure at the site, mechanical pressure can be removed.

Thus, bleeding during traditional surgical procedures, which often occurs as a result of cutting minor arteries, veins and capillaries, generally can be stanched by direct manual application of a hemostatic material, such as collagen, and digital pressure through the surgical opening. However, when surgery is performed by a laparoscopic procedure, for example, when removing a gall bladder, access to the bleeding site is far more restricted.

SUMMARY OF THE INVENTION

Therefore, it is an object of the present invention to provide an improved hemostat delivery system for use in a laparoscopic procedure.

It is another object of the present invention to provide a laparoscopic hemostat system and method that reduces or eliminates the need for cauterization in laparoscopic procedures.

It is yet another object of the present invention to provide a delivery system and method for effecting hemostasis at an internal surgery site using a nondestructive resorbant hemostatic material.

It is a further object of the present invention to provide a system and method for applying a hemostatic material, such as collagen, directly to an internal site of bleeding.

These and other objects and advantages are achieved by the system and method of the present invention, in which a hemostat delivery system is used to advance a plug of hemostatic material through a laparoscopic cannula and mechanically apply it directly to the site of bleeding. The laparoscopic hemostat delivery system generally comprises a sheath having a proximal end, a distal end and a continuous lumen therethrough, and an applicator having a plunger slidably disposable within the sheath lumen. A plug of hemostatic material may be preloaded within the sheath lumen.

In operation, the sheath is inserted through a working channel of a laparoscopic cannula and is thereby directed to an internal surgical site where there is bleeding. The plug of hemostatic material is advanced to the site of bleeding by applying pressure to the applicator plunger. The hemostatic plug preferably is composed of a resorbable hemostatic material, such as collagen. Hemostasis is initiated by mechanical pressure, but shortly thereafter self-sustaining hemostasis, which results from the interaction between the hemostatic material and the site tissue, takes over.

BRIEF DESCRIPTION OF THE DRAWING

A more complete appreciation of the present invention and the many attendant advantages thereof readily will be apparent with reference to the following detailed description of a preferred embodiment of the invention together with the accompanying drawing, wherein.

DETAILED DESCRIPTION OF A PREFERRED EMBODIMENT

Figure 1:
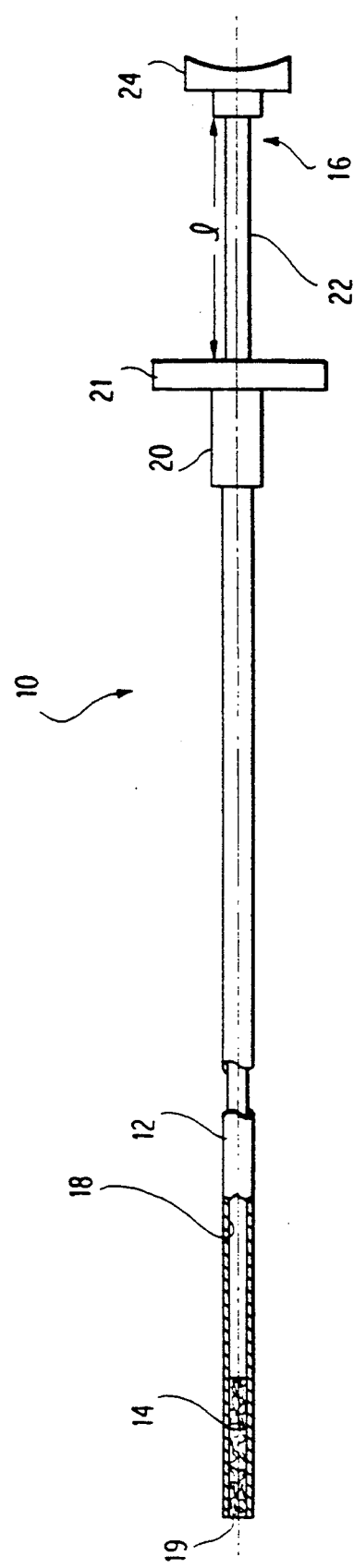
FIG. 1 illustrates in plan view a laparoscopic hemostat system of the present invention, partly cut away to show in cross-section its constituent components, including a sheath, an applicator plunger and a preloaded hemostatic plug slidably disposed in the sheath.

Referring now to the drawing, FIG. 1 illustrates a preferred embodiment of a laparoscopic hemostat system 10 of the present invention As shown in FIG. 1, laparoscopic hemostat system 10 generally comprises a sheath 12, a plug of hemostatic material 14 and an applicator 16.

Sheath 12 generally comprises a tubular housing 18, defining a lumen 19, and a hub 20 disposed at the proximal end of housing 18. The hub 20 is provided, at its proximal end, with a flange 21 which is designed to serve as a finger grip. Sheath 12 may be composed of a pliable biocompatible material suitable for use in surgical procedures (e.g., a gamma-sterilizable material), and is preferably composed of a durable plastic material. For example, tubular housing 18 may be composed of TEFLON, polyethylene or other suitable plastic used in surgical devices, or metal. The latter two materials may be provided with lubricated lumens to reduce friction of collagen or hemostatic material being pushed through to the distal end.

The outer diameter and cross-sectional configuration of housing 18 are chosen so as to permit sliding passage, with minimal clearance, through a working or other channel of a laparoscopic cannula. In the preferred embodiment, the sheath is circular in cross-section, with the outer diameter being in the range of between about 3 and about 10 mm, most preferably either about 5 mm or 10 mm. These dimensions generally are suitable for existing laparoscopic cannulae The actual sizing, however, will vary depending on the procedure and circumstance, as will be readily appreciated by those skilled in the art.

Applicator 16 generally comprises a cylindrical plunger 22 and a thumb plate 24 disposed at its proximal end. Plunger 16 will generally be fabricated of a pliable biocompatible material suitable for use in surgical procedures (e.g., a gamma-sterilizable material), and is preferably composed of a plastic material, most desirably polyethylene. The sizing of the outer diameter of plunger 22 is selected so that it has a cross-section and configuration that permits sliding passage with minimal clearance through lumen 19 of tubular housing 18. The length of plunger 22 is selected so that when thumb plate 24 abuts finger grip 21 of hub 20, the distal end of plunger 22 will align with the distal end of sheath 12. In the preferred embodiment, plunger 22 is composed of a solid plastic material with a blunt distal end for engaging and advancing hemostatic plug 14 through and out of sheath 12.

Hemostatic plug 14 may be composed of any biocompatible hemostatic material, preferably a resorbable hemostatic material, and most preferably collagen. The hemostatic material may be in any form which is suitable for delivery through the sheath. For example, it may be in the form of a loose fibrous material, (e.g., a cottony or fleece-like material), a sponge, a paste, a folded membrane or a woven or non-woven sheet. An example of a commercially available collagen sheet material is NOVACOL, manufactured by Datascope, the assignee of this patent application. Other commercially available hemostatic materials which may be suitable for use in practicing the instant invention are AVITENE, a powder or non-woven web manufactured by MedChem Products and SURGICEL, a product of Johnson & Johnson.

Laparoscopic hemostat system 10 may be used with existing laparoscopic cannulae (not shown). As noted above, a laparoscopic procedure generally involves use of several cannulae, each acting as a channel through which access can be gained to the procedure site. There may be a light/viewing channel, a gas delivery channel and two or more additional working channels. When, during a laparoscopic surgical procedure, tissue or blood vessels are cut, thereby causing bleeding, the laparoscopic hemostat system 10 of the present invention can be inserted and passed through one of the working channels to the site of bleeding. Alternatively, hemostat 10 could be preloaded in one of the laparoscopic cannulae prior to the latter's insertion into the patient's body.

The system of the present invention can be assembled as needed or it can be preassembled. When it is to be assembled on site, the physician would first determine that the need for it exists. The hemostatic material, preferably in the nature of a collagen plug, would then be inserted into lumen 19, either through the opening in the distal end or through the opening in the proximal end of the sheath. If the loading is done through the proximal end, it would be followed by insertion of the plunger 22. If it is loaded through the distal end, plunger 22 would most likely be inserted from the proximal end first.

Alternatively, the entire system could be preassembled, with both the plunger and the hemostatic material resident in lumen 19 all ready for use.

According to the procedure of the present invention, the surgeon positions the distal end of sheath 12 at the bleeding site and applies pressure to thumb plate 24 of applicator 16. As plunger 22 slides through sheath 12 it advances the hemostatic plug 14 until the latter exits from the sheath. Note, the length "1" of the proximal end of the plunger extending from the proximal end of sheath 12 may be preregistered for the exact length of the hemostatic plug 14, so that the surgeon can accurately determine when hemostatic plug 14 is just fully within the distal end of sheath 12. When thumb plate 24 of applicator 16 abuts hub 20, the physician knows that plug 14 has been pushed entirely out of lumen 19 and that the distal end of plunger 22 is substantially flush with the distal end of sheath 12. As the advancing hemostatic plug 14 engages the tissue site, i.e., the site of bleeding, the physician will encounter resistance at thumb plate 24. He then maintains axial pressure so as to hold hemostatic plug 14 against the site of bleeding. Thus, hemostatic plug 14 is mechanically held against the site of bleeding to achieve immediate hemostasis. As the hemostatic material begins to interact with bleeding tissue, self-sustaining hemostasis begins to take over until mechanical pressure is no longer needed.

While plug 14 may be composed of any resorbable material, collagen is believed most suitable. The physical form of plug 14 may vary widely, with the one selected by the physician being dependent on the circumstances of the case. For example, loose, long-fibered collagen may be compacted within the distal end of tubular housing 18 to form plug 14. In another example, a sheet of long fibered collagen pad (e.g., NOVACOL, manufactured by Datascope) may be rolled up to form a cylindrical plug loadable within the distal end of housing 18. In another example, a sheet of thin, flexible, integrated collagen also can be rolled up to form a cylindrical plug. Generally, in the case of collagen, approximately 1/24 to 1/10 gram may be used. In the case of a sheet of collagen, or other hemostatic material, for example, a 2×3 inch sheet may be rolled up to form the cylindrical plug. In other cases, oxygenated cellulose may be used. It will be understood that those skilled in the art readily will be able to determine the type and amount of hemostatic material sufficient for effecting hemostasis.

In yet another embodiment, hemostatic plug 14 may comprise a combination of one or more types of hemostatic material (e.g., loose fibrous, sponge, paste, sheet, etc.). For example, hemostatic plug 14 may comprise a sponge portion and a loose fibrous portion, wherein the loose fibrous portion is disposed at the most distal end of sheath 12. Alternatively, hemostatic plug 14 could comprise a sheet portion and a sponge portion, wherein the sheet portion is disposed at the most distal end of sheath 12. It will be appreciated that this arrangement would first provide a sheet of hemostatic material for covering a surface site of bleeding, followed by a backing (sponge) for applying pressure over the entire surface of the bleeding site. Such two (or more) component plugs may be joined together or may be structurally separate and independent. Other combinations and their advantages readily will be apparent to those skilled in the art.

As those skilled in the art know, when loose, fleece-like fibrous collagen encounters a pool of blood it tends to disintegrate almost immediately. Obviously, once disintegrated it cannot function properly to effect hemostasis at the site of bleeding. Therefore, it is generally advantageous if the loose fibrous material has been tamped down or otherwise compressed.

It should also be readily apparent from the above description that more than one plug could be used. If the physician were to decide to use more than one plug, (s)he need only remove plunger 22, insert a second plug (of the same or different material) into the proximal end of lumen 19 and then reinsert plunger 22 behind it. Alternatively, the entire system 10 could be removed and replaced with a second one which has been pre-loaded and is ready for immediate use. Thus, it will be appreciated that a second, third, etc., hemostatic plug 14 may be delivered and applied to the site of bleeding to effect hemostasis.

Numerous other embodiments and modifications will be apparent to those skilled in the art and it will be appreciated that the above description of a preferred embodiment is illustrative only. It is not intended to limit the scope of the present invention, which is defined by the following claims.

What is claimed is:

1. A method for directly applying a plug of hemostatic material against an internal vascular tissue site of a patient during a laparoscopic procedure, comprising the steps of, charging a hollow sheath having a distal end and a proximal end with a plug of hemostatic material, passing the distal end of said sheath through a channel of a laparoscopic cannula, and guiding the distal end of said sheath to a position facing the vascular tissue site, passing a plunger through a lumen of said hollow sheath, thereby advancing the plug of hemostatic material in said lumen, such that a portion of the plug of hemostatic material exits the distal end of the hollow sheath, and mechanically applying with pressure the distally extending portion of the plug of hemostatic material against the vascular tissue site to effect rapid hemostasis.

2. The method according to claim 1, further comprising the steps of, forming said plug of hemostatic material of a predetermined amount, and passing said plunger through said lumen to a predetermined registration mark, thereby disposing said plunger and plug of hemostatic material in a preselected location in said sheath.

3. The method according to claim 1, further comprising the steps of, maintaining mechanical pressure against said vascular tissue until self-sustaining hemostasis has occurred; and then removing said mechanical pressure.

4. The method according to claim 1, further comprising the steps of, slowly lessening the amount of mechanical pressure applied against the vascular tissue as said hemostatic material begins to interact with said vascular tissue, and removing said mechanical pressure when said interaction between said hemostatic material and said vascular tissue has produces self-sustaining hemostasis.

5. A delivery system for use in a medical procedure including a method according to claim 1, the system comprising:

a sheath having a proximal end, a distal end and a lumen therethrough, and having a cross-section and configuration that permits sliding passage thereof through the channel of the laparoscopic cannula, a plug of hemostatic material in said sheath lumen, means for advancing said plug of hemostatic material through said sheath lumen, and means for mechanically applying with pressure said plug of hemostatic material against vascular tissue at said site to effect hemostasis.

6. The delivery system according to claim 5, wherein said means for advancing and mechanically applying said plug of hemostatic material comprises an applicator including a plunger having a cross-section and configuration that permits sliding passage thereof through said sheath lumen with minimal clearance.

7. The delivery system according to claim 6, wherein said applicator further comprises a thumb plate.

8. The delivery system according to claim 6, wherein said sheath further comprises a flange disposed at said proximal end and forming a finger grip.

9. A delivery system for use in a medical procedure including a method according to claim 1, the system comprising:

a sheath having a proximal end, a distal end and a lumen therethrough, and having a cross-section and configuration that permits sliding passage thereof through the channel of the laparoscopic cannula, a plug of hemostatic material composed primarily of collagen, means for advancing said plug of hemostatic material through said sheath lumen, and means for mechanically applying with pressure said plug of hemostatic material against vascular tissue at said site to effect hemostasis.

10. A delivery system for use in a medical procedure including a method according to claim 1, the system comprising:

a sheath having a proximal end, a distal end and a lumen therethrough, and having a cross-section and configuration that permits sliding passage thereof through the channel of the laparoscopic cannula, a plug of hemostatic material in the form of compacted loose fibers, means for advancing said plug of hemostatic material through said sheath lumen, and means for mechanically applying with pressure said plug of hemostatic material against vascular tissue at said site.

11. The delivery system according to claim 5, wherein said plug of hemostatic material is in the form of a compressed sponge.

12. A delivery system for use in a medical procedure including a method according to claim 1, the system comprising:
  a sheath having a proximal end, a distal end and a lumen therethrough, and having a cross-section and configuration that permits sliding passage thereof through the channel of the laparoscopic cannula,
  a plug of hemostatic material in the form of a sheet,
  means for advancing said plug of hemostatic material through said sheath lumen, and
  means for mechanically applying with pressure said plug of hemostatic material against vascular tissue at said site to effect hemostasis.

13. The delivery system according to claim 5, wherein said plug of hemostatic material includes a hemostatic paste.

14. The delivery system according to claim 5, wherein said plug of hemostatic material is composed of at least two components selected from the group consisting of compressed loose fibers, a powder, a sponge, a paste and a sheet.

15. The delivery system according to claim 5, wherein said plug of hemostatic material is resorbable.

* * * * *